United States Patent [19]

Allen et al.

[11] 4,269,507
[45] May 26, 1981

[54] METHOD AND APPARATUS FOR PULVERIZING SOLID MATERIALS WITH A GRINDSTONE AND INJECTING PARTICLES THEREOF INTO A FLAME FOR ANALYSIS

[75] Inventors: Jonathan Allen, Hopewell; Robert K. Gould, East Windsor Township, Mercer County, both of N.J.

[73] Assignee: Aerochem Research Laboratories, Inc., Princeton, N.J.

[21] Appl. No.: 81,938

[22] Filed: Oct. 4, 1979

[51] Int. Cl.³ .......................... G01N 1/22; G01N 21/72
[52] U.S. Cl. ................................. 356/36; 73/421 R; 250/288; 356/315
[58] Field of Search .................... 356/36, 315, 316; 250/288, 304; 73/421 R

[56] References Cited

U.S. PATENT DOCUMENTS

| 3,163,699 | 12/1964 | Staunton | 356/315 |
| 3,625,614 | 12/1971 | Herrmann et al. | 356/315 |
| 3,791,743 | 2/1974 | Cody et al. | 356/36 X |
| 3,957,374 | 5/1976 | Kriese et al. | 356/36 X |

OTHER PUBLICATIONS

"Molecular Analysis by Mass Spectrometry"; Vigon, Jr.; Science, vol. 205, 13 Jul. 1979; pp. 151-195.

Primary Examiner—Vincent P. McGraw
Attorney, Agent, or Firm—Richard C. Woodbridge

[57] ABSTRACT

A grinding wheel is used to pulverize solid test samples and propel particles thereof into a flame for analysis by an instrument such as a mass spectrometer. The sample is attached to one end of a pivoted lever arm. The other end of the lever arm is connected to a solenoid. Activation of the solenoid brings the sample into contact with the rotating grinding wheel. The solid particles produced by the wheel are propelled into the flame through a slot in an intermediate draft shield. The sampling cone of a conventional mass spectrometer or similar instrument may be placed in the flame to analyze the nature of the test materials. The device may also be used to inject test particles into the air or gas feed stream ahead of the flame if desired.

14 Claims, 3 Drawing Figures

METHOD AND APPARATUS FOR PULVERIZING SOLID MATERIALS WITH A GRINDSTONE AND INJECTING PARTICLES THEREOF INTO A FLAME FOR ANALYSIS

BACKGROUND OF THE INVENTION

1. Field of the Invention

This invention relates to an analytical device for flame analysis of solid materials.

2. Description of the Prior Art

Mass spectrometers are used extensively as tools for molecular analysis. In negative ion flame mass spectrometry a sample of a gas or aspirated liquid is typically introduced into a flame and subsequently analyzed by the mass spectrometer. A good general description of the uses of mass spectrometers may be found in an article entitled "Molecular Analysis by Mass Spectrometry" by Woodfin V. Ligon, Jr. which appeared in the July 13, 1979, Volume 205, No. 4402 edition of SCIENCE. U.S. Pat. Nos. 3,163,699 and 3,625,614 both describe methods by which liquid samples may be analyzed.

While it is relatively easy to introduce a gas or liquid into a flame, it is considerably more difficult to introduce a solid. Under some circumstances it is possible to dissolve the solid materials in a liquid medium. However, many materials do not adequately lend themselves to that technique. One approach for analyzing samples of dust solid is described in U.S. Pat. No. 3,957,374.

The present invention allows a solid sample to be introduced as particles directly into a flame or into the air or gas line that feeds the flame. The use of grinding wheels and grinding belts is fairly well known in the tool sharpening arts. The present invention concerns a highly original grinding wheel device that can be adjusted to produce a continuous stream of solid particles that lend themselves to flame analysis.

SUMMARY OF THE INVENTION

Briefly described the invention comprises a method and apparatus for pulverizing hard solids and feeding them into a flame for testing. A small grindstone driven by an electric motor is set close to the flame of a burner. The hard specimen is secured in a holder at one end of a pivoted lever arm. The other end of the lever arm is connected through a pressure spring to a solenoid. A weak return spring is located between the sample holder and the pivot point to withdraw the sample from the grinding wheel when the solenoid is de-activated. Activation of the solenoid brings the sample into grinding contact with the rotating wheel. Particles produced by the rotating wheel are naturally propelled into the analytical flame. The size and volume of material can be reliably controlled by changing the location of the solenoid and controlling the speed of the grinding wheel. According to an alternative embodiment of the invention the particles may be injected into the air/gas stream which feeds the flame.

The technique can be helpful for flame spectroscopy, photometric analysis and flame ionization mass spectrometry. It permits the introduction into the flame of large quantities of specimens without the need for dissolving the material beforehand. It is especially valuable in analyzing marginally soluble or insoluble substances and in testing compounds which might be altered by dissolving.

These and other features of the invention will be more fully understood with reference to the following drawings and detailed description of the invention.

DETAILED DESCRIPTION OF THE INVENTION

During the course of this description like numbers will be used to indicate like elements according to the three different figures which illustrate the invention.

Figure 1:
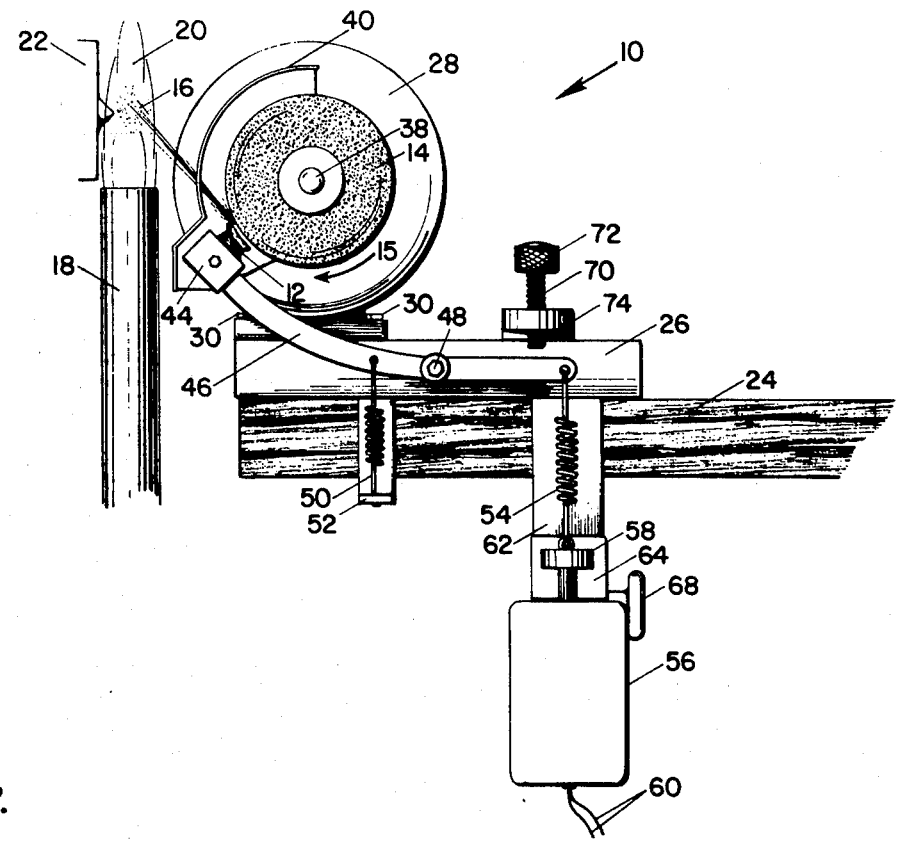
FIG. 1 is a side elevational view of the preferred embodiment of the invention.
Figure 2:
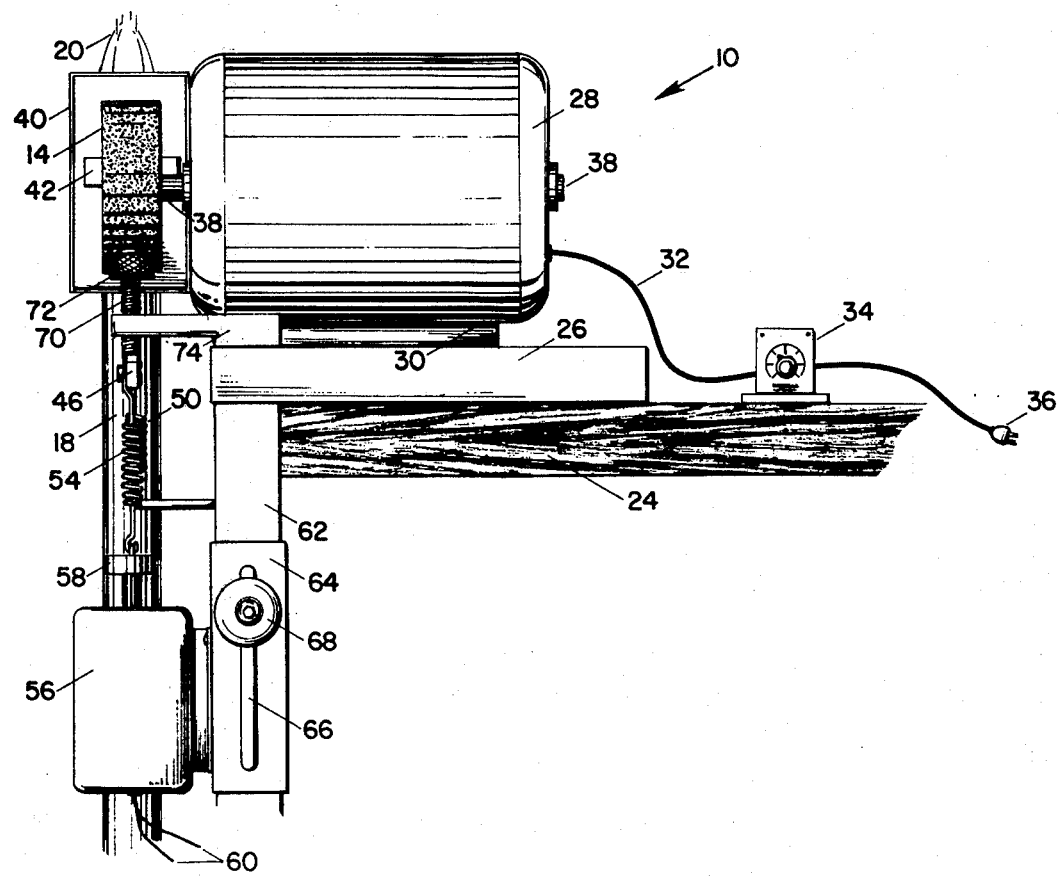
FIG. 2 is a rear elevational view of the preferred embodiment of the invention illustrated in FIG. 1.

As shown in FIGS. 1 and 2, the invention 10 basically comprises a grinding means 14 and a pressure means which bring a hard solid sample 12 into grinding contact with the grinding means 14. The grinding means preferably comprises a small grindstone 14 which rotates in the direction of arrow 15. The wheel 14 should be a small one similar to those used on grinders for making models or those used on flexible shaft machines. In size it can range from 1.5 to 4 centimeters in diameter. A thickness of 1 centimeter is preferable. The distance from the wheel 14 to flame 20 should be comparable to the radius of wheel 14. Accordingly, a distance of 0.75 to 2 centimeters would be desirable. The flame 20 is provided by a conventional laboratory burner 18. The distance from the flame 20 to the wheel 14 should be close enough to insure that essentially all of the pulverized specimen particles 16 enter the flame 20 yet the distance should be far enough so that the air draft stirred up by the wheel 14 does not unduly disturb the flame 20. The particles 16 that enter the flame are ionized and analyzed by an instrument such as a mass spectrometer. A mass spectrometer cone 22 is illustrated in FIG. 1 as being typical of the type that may be employed with this invention. The invention also lends itself to flame spectroscopy and photometric analysis as well as flame ionization mass spectrometry.

The apparatus 10 is typically attached to a bench 24 or similar surface. A horizontal base 26 serves as a mounting platform for drive motor 28 and the other elements of the invention. Bolts 30 secure the motor 28 to the apparatus base 26. Power is supplied to the motor through a conventional cord 32 and plug 36. A motor speed control 34 may be inserted in the line 32 to change the speed of the motor. Grinding wheel 14 is mounted on motor shaft 38 using standard grindstone mounting techniques.

A judiciously placed guard or draft shield 40 is placed between the grindstone 14 and the flame 20. A slot 42 permits the particles 16 to enter the flame. The draft shield 40 prevents the flame from becoming disturbed by the rapid rotation of wheel 14. The preferred grindstone speed will depend upon the materials involved and the details of the experimental setup. A range of 3,000 to 12,000 RPM is reasonable and can be varied depending upon the setting of motor control 34. Higher speeds would be more readily obtainable on smaller diameter wheels. The resulting tangential velocities would therefore range from 500 to 1,000 centimeters per second (5–10 m/sec).

The pressure means essentially comprises a sample holder 44, lever arm 46, pivot bolt 48 and solenoid 56. The sample holder 44 is located at one end of pivoted lever arm 46. A pivot bolt 48 is located in the intermediate section of lever arm 46. Solenoid 56 is attached through a pressure spring 54 to the end of the lever arm 46 furtherest removed from sample holder 44. A weak return spring 50 is attached to lever arm 46 at a point between the sample holder 44 and the pivot bolt 48. The other end of the weak return spring 50 is connected to a mounting bracket 52 attached to base plate 26. Solenoid 56 includes a plunger element 58 which is attached to pressure spring 54. Activating electrical power is supplied through electrical lines 60 to govern the motion of plunger 58. Solenoid 56 is mounted on a slide 64 which in turn partially surrounds a solenoid mounting bracket 62 attached to base 26.

The tension on spring 54 can be modified by drawing the solenoid 56 downward and locking it in position by means of threaded locking screw 68. The slide locking screw 68 passes through the slot 66 in slide 64 and is threadably received in the solenoid mounting bracket 62. Locking screw 68 includes a shoulder, not illustrated, which impinges against the sides of the slot 66. The pressure of the hard specimen 12 against the wheel 14 can be modified either by changing the spring constant of pressure spring 54 or by changing the location of solenoid 56. The specimen 12 should preferably press against the wheel with a force of 0.1 to 1.0 newtons. Increasing the force tends to yield larger particles of a given material.

A return stop screw 70 serves to limit the travel of lever arm 46. Stop screw 70 is threadably received in mounting bracket 74 and includes a knurled head 72. By manually turning head 72 it is possible to adjust the distance between the end of the shaft of stop screw 70 and the end of lever arm 46 furtherest removed from the specimen 12. In the foregoing manner the stop screw 70 dampens out undesirable oscillations and determines the distance that specimen 12 will be from grinding wheel 14 when solenoid 56 is deactivated.

Figure 3:
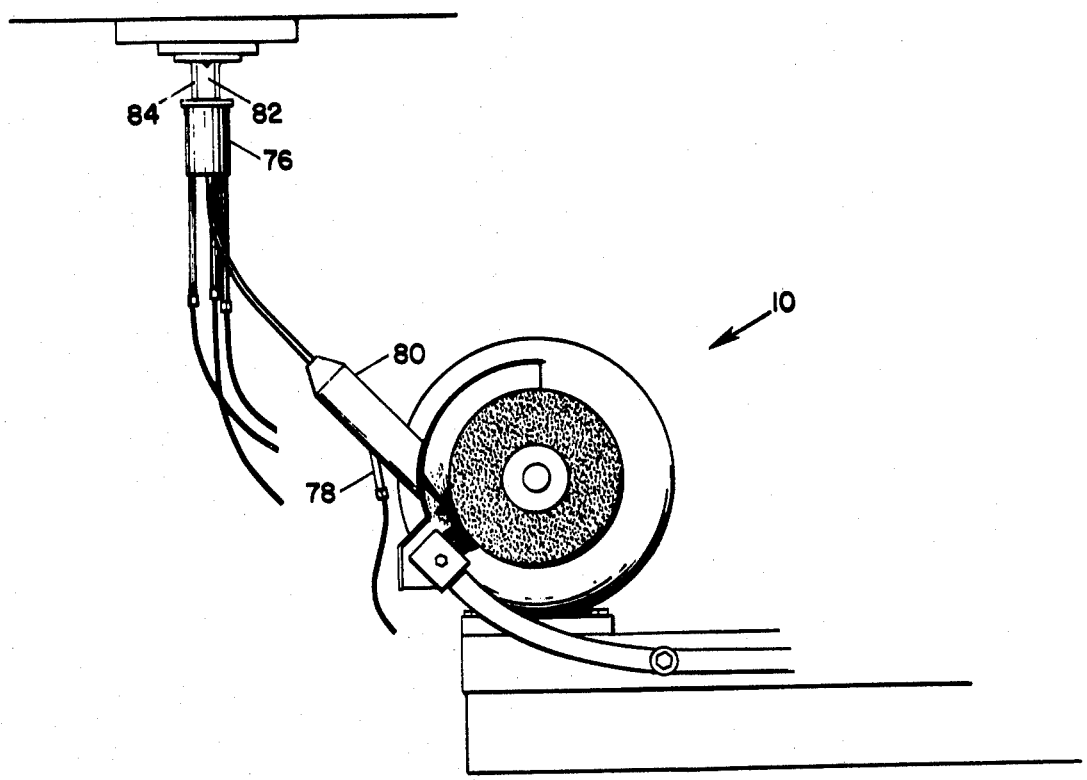
FIG. 3 is an alternative embodiment of the invention in which the specimen particles are injected into the air/gas feed stream ahead of the flame.

An alternative embodiment of the present invention is illustrated in FIG. 3. According to that embodiment the burner 76 includes an inner flame 82 and an outer flame 84. Outer flame 84 is fed by air feed line 78. Particles from the device 10 are fed through a particle hood 80 directly into the gas flow which feeds outer flame 84. Accordingly the pulverized, ground specimen particles 16 are injected into the air stream well before they reach the flames. This is in contrast to the preferred embodiment of FIGS. 1 and 2 wherein the ground particles are injected directly into the flame. Accordingly, as a general proposition there is some flexibility in the invention so that particle injection can occur ahead of the flame provided that the air or gas flow velocities are sufficient to carry the particles along. The compound inner and outer flame device illustrated in FIG. 3 is described in more complete detail in a copending application entitled Flame Sampling Apparatus and Method by Dr. Hartwell Forrest Calcote. According to that invention the outer flame 82 is seeded with the material to be analyzed. The cone of a mass spectrometer sits within inner flame 82 and samples the negative ions produced in the outer flame 84. The technique described in this invention for producing and analyzing solid particles lends itself especially well to the invention further described in the foregoing copending application.

According to the preferred embodiment the flame 20 could be any of the commonly used analytical flames such as hydrogen with air or oxygen, methane, or if hydrogen is to be avoided, carbon monoxide. The grindstone may, from a mechanical standpoint, be made of any rough material substantially harder than the specimen. However, in order to avoid chemical contamination or interference, the material of the wheel 14 must be selected so that particles of the wheel 14 that dislodge with the specimen do not confuse the analysis. Accordingly that could require abrasives made from chemically pure alumina, silicon carbide, etc. and fabricated by sintering or vitrified bonding. The grindstone pulverization method and apparatus described in this disclosure could be applicable to almost any hard substance. However, it would most likely find special application in analyzing the silicon used in the semiconductor industry and in determining the impurity level in artificially-grown crystals. Mineralogists and geologists might also find this method and apparatus useful in determining the composition of specimens and ore samples.

The flame 20 is preferably chosen to vaporize and to react or ionize the specimen for spectroscopic or mass-spectrometric analysis.

The apparatus 10 just described operates in the following manner. The specimen holder 44 located at a first end of lever arm 46 holds the sample material 12 to be analyzed. The lever arm 46 is pivoted through its intermediate section around pivot bolt 48. Accordingly, the specimen 12 may be brought into contact with grinding wheel 14 as needed. The maximum distance from the grinding wheel 14 to the sample 12 is set by the return stop screw 70. Under idling conditions the relatively weak return spring 50 holds the specimen 12 off of the wheel 14. In order to feed the specimen 12 to the wheel 14 it is first necessary to energize the solenoid 56 through electrical leads 60. Activation of the solenoid 56 draws down on plunger 58 which in turn acts upon pressure spring 54 to overcome the resistance of return spring 50 and press the specimen 12 against the wheel 14. It is possible to adjust the specimen pressure by moving solenoid 56 up and down on a sliding mount 64. The specimen feed pressure may also be modified by substituting springs with different spring constants for pressure spring 54. The draft shield 40 serves to prevent the eddy air currents generated by the revolving grindstone 14 from disturbing the even burning of flame 20. Slot 42 in shield 40 permits the particles 16 to pass therethrough. However, the shield otherwise blocks off the air currents stirred up by the rapidly spinning wheel 14. Motor 28 may be of any type with sufficient speed and torque to drive wheel 14 at several thousands RPM against the resistance due to the friction of specimen 12 against grindstone 14. A conventional motor speed control 34 may be employed to vary the speed of motor 28 as required.

While the invention has been described with reference to the preferred embodiment thereof, it will be appreciated by those of ordinary skill in the art that various changes may be made to the structure and method of the invention without departing from the spirit and scope thereof.

We claim:

1. In a test apparatus for analyzing solid materials including a flame analyzing instrument and a flow of combustible gas culminating in a flame, the improvement comprising:

rotating grinding means for pulverizing a solid sample of material and propelling ground particles thereof into said combustible gas; and, pressure means for pressing said solid sample against said grinding means.

2. The apparatus of claim 1 further comprising:

a drive motor attached to said grinding means for rotating said grinding means.

3. The apparatus of claim 2 wherein said pressure means comprises:

a sample holding means for holding said solid sample;

a lever means having a first end connected to said sample holding means, an intermediate pivot section and a second end removed from said first end;

a pivot means connected to said intermediate pivot section; and, an activation means connected to said second end, of said lever means, wherein activation of said activation means causes said sample to come into contact with said grinding means.

4. The apparatus of claim 3 further including:

a draft shield located between said grinding means and said flame, said shield including a slot therein through which said ground particles can pass.

5. The apparatus of claim 4 further including:

a return spring attached to said lever means between said first end and said intermediate pivot section thereof.

6. The apparatus of claim 5 further including:

a pressure spring attached between said activation means and said second end of said lever means.

7. The apparatus of claim 6 further including:

a slide means attached to said activation means for changing the position of said activation means and thereby changing the pressure of said sample against said grinding means.

8. The apparatus of claim 7 further including:

a locking means for locking said slide means in a specific location.

9. The apparatus of claim 8 wherein said activation means comprises an electrical solenoid; and, said locking means comprises a screw means which passes through a slot in said slide means and is threadably received in a relatively unmovable frame on the opposite side thereof.

10. The apparatus of claim 9 further including:

a stop means to limit the movement of said second end of said lever means.

11. The apparatus of claim 10 wherein said grinding means comprises a grinding wheel.

12. The apparatus of claim 11 wherein said particles are introduced directly into said flame.

13. The apparatus of claim 12 wherein said particles are introduced into said combustible gas ahead of said flame.

14. A method for analyzing solid materials comprising the steps of:

grinding a sample of said solid material on a rotating medium that produces solid sample particles and propels said solid sample particles away from said sample of solid material;

combining said propelled solid sample particles with a combustible gas;

combusting the combination of solid sample particles and gas in a flame; and, analyzing said flame with a test instrument.

* * * * *